United States Patent [19]
Thornton et al.

[11] Patent Number: 5,330,487
[45] Date of Patent: Jul. 19, 1994

[54] DRIVE MECHANISM FOR SURGICAL INSTRUMENTS

[75] Inventors: Curtis W. Thornton, Cary; Thomas W. Ruckdeschel, Apex, both of N.C.

[73] Assignee: TFI Acquistion Corp., Research Triangle Park, N.C.

[21] Appl. No.: 991,891

[22] Filed: Dec. 17, 1992

[51] Int. Cl.$^5$ .............................................. A61B 17/12
[52] U.S. Cl. .................................................... 606/143
[58] Field of Search .................. 606/143, 142, 139; 227/175, 176, 177, 181, 182, 19, 901

[56] References Cited

U.S. PATENT DOCUMENTS

| | | | |
|---|---|---|---|
| 4,196,836 | 4/1980 | Becht | 606/143 |
| 4,662,374 | 5/1987 | Blake, III | 606/143 |
| 4,712,549 | 12/1987 | Peters et al. | 606/143 |
| 5,112,343 | 5/1992 | Thornton | 606/143 |

FOREIGN PATENT DOCUMENTS

| | | | |
|---|---|---|---|
| 112980 | 7/1984 | European Pat. Off. | 606/143 |
| 406724 | 1/1991 | European Pat. Off. | 606/139 |

Primary Examiner—Tamara L. Graysay
Attorney, Agent, or Firm—Gene Warzecha; Steve Rosenblatt

[57] ABSTRACT

A surgical instrument for applying a ligating device to a surgical work site. The instrument is provided with a power subassembly which provides the power by which the ligating device is placed into proper position for being applied to the work site. In one embodiment, the instrument is a hemostatic clip applier and the power subassembly feeds the clips into position between the jaws of the applier which are then closed by squeezing the applier handles.

18 Claims, 20 Drawing Sheets

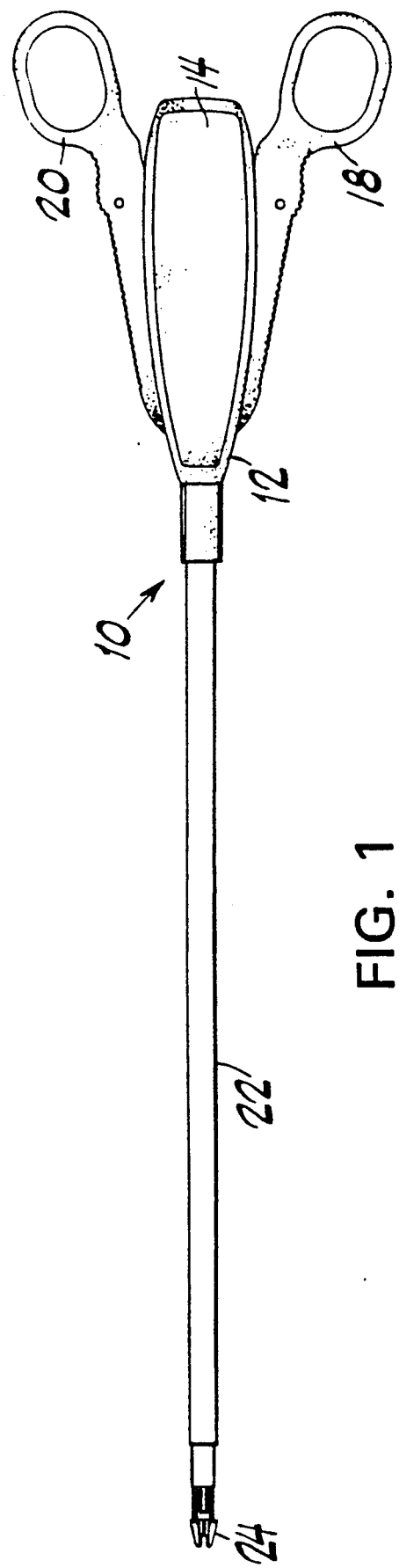
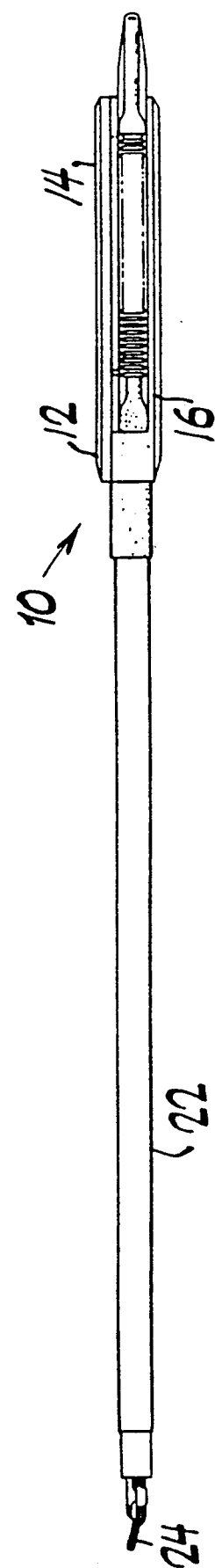
FIG. 1
FIG. 2

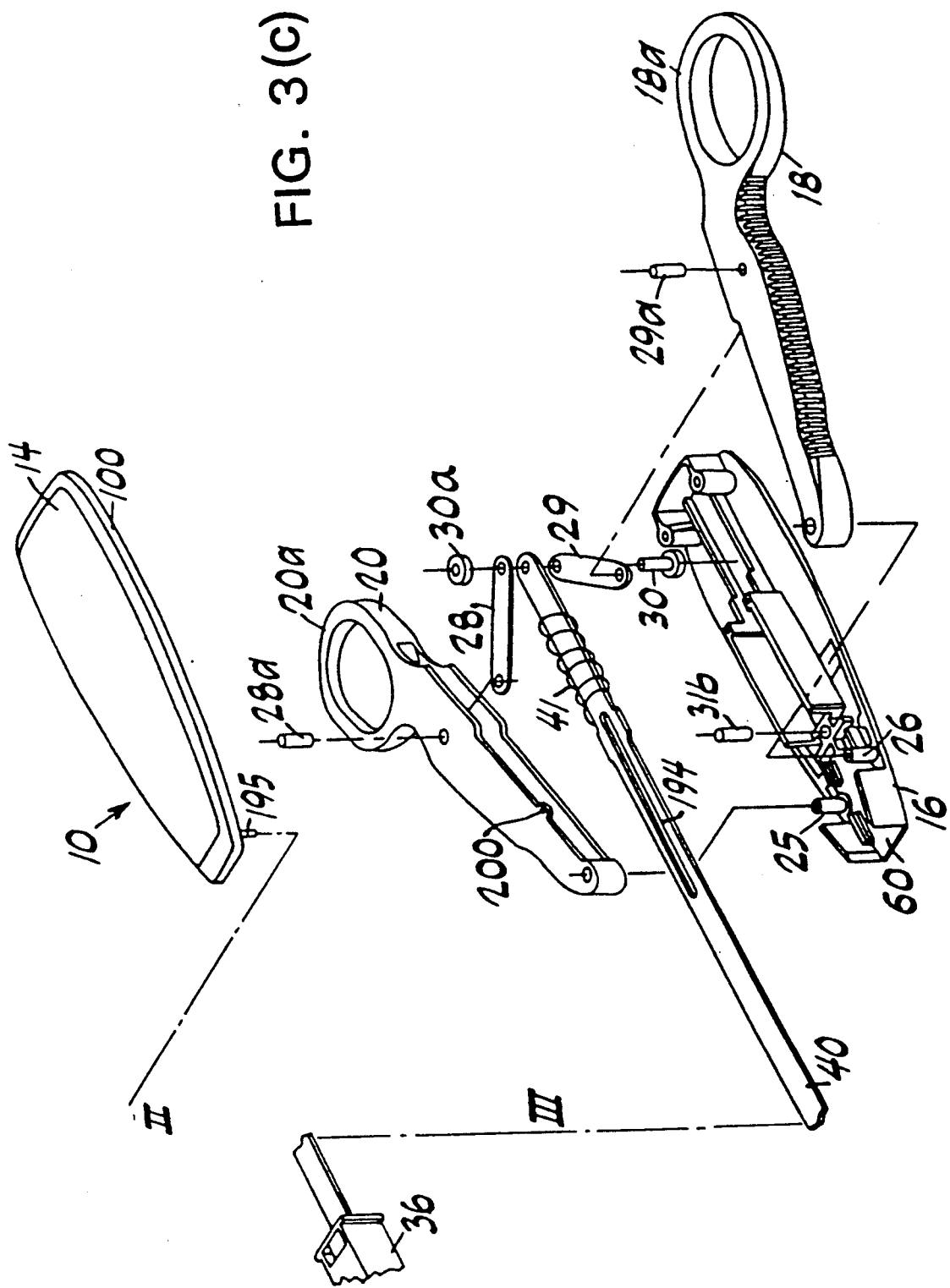

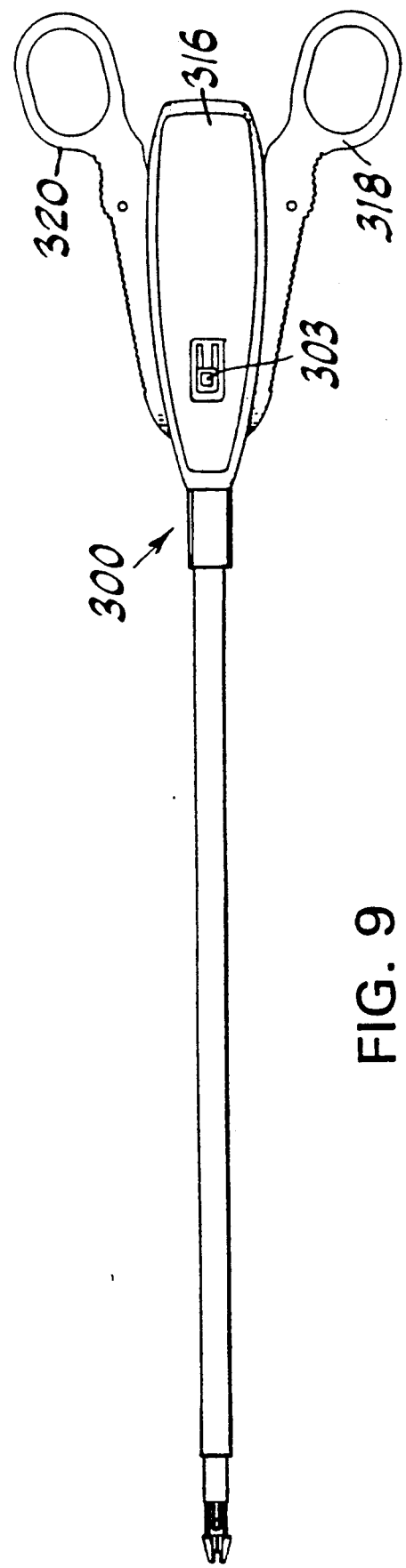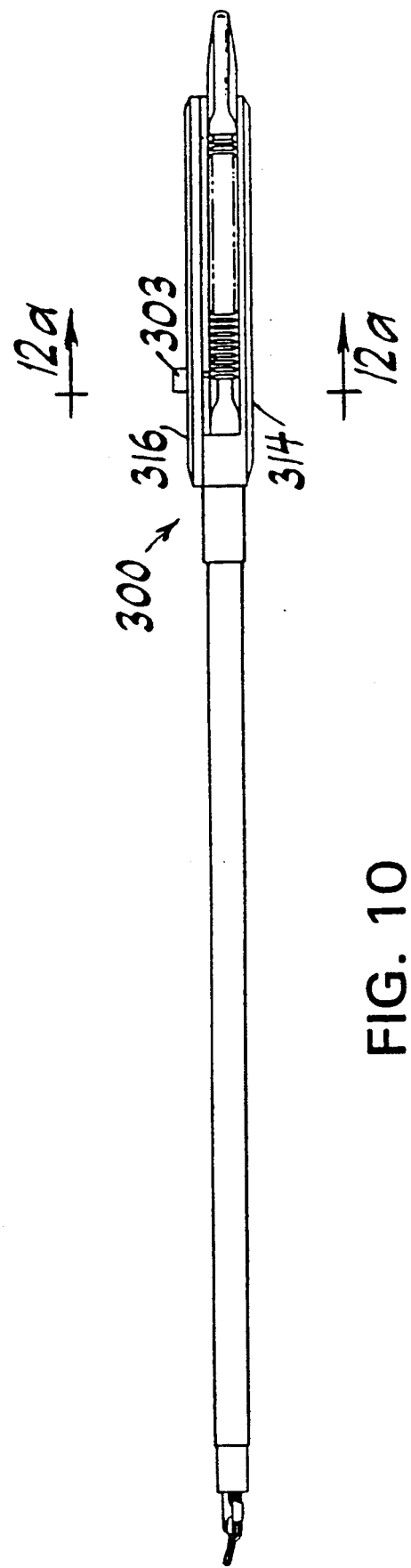

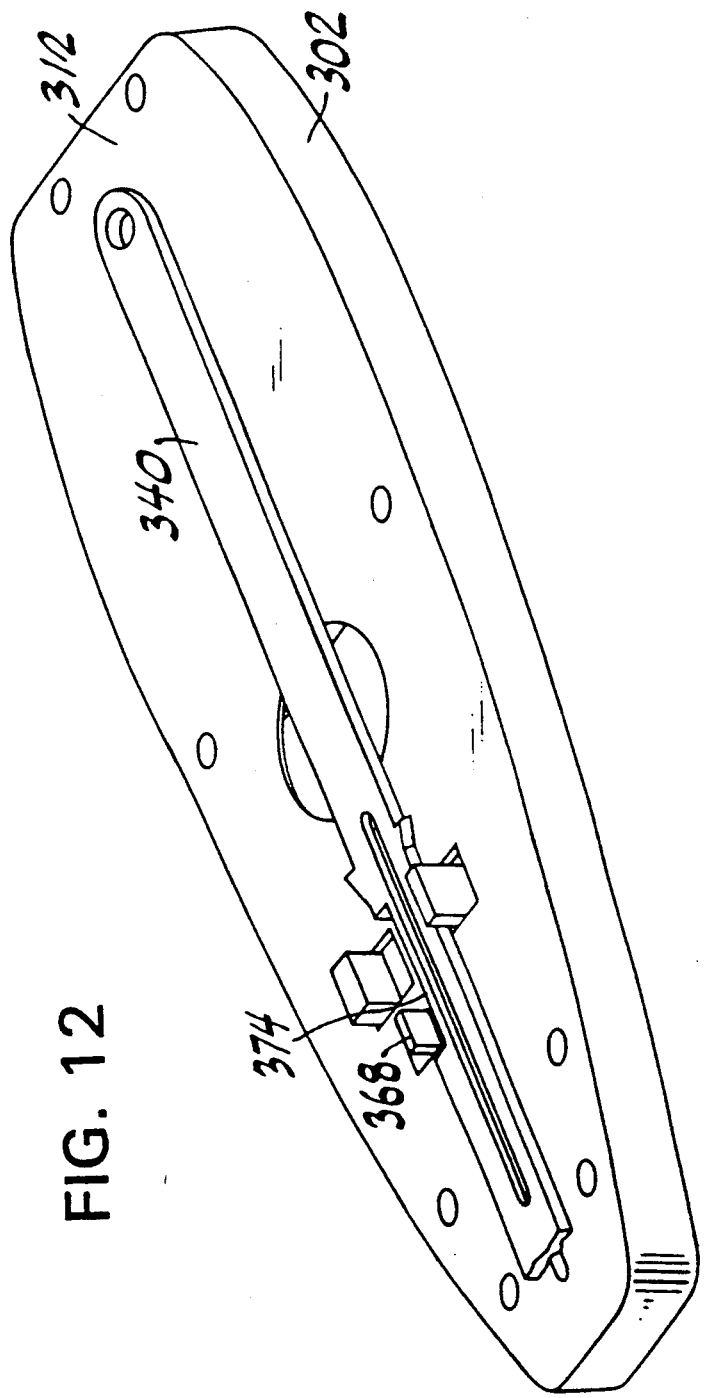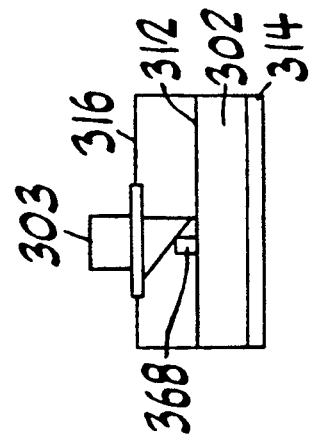
FIG. 12
FIG. 12(a)

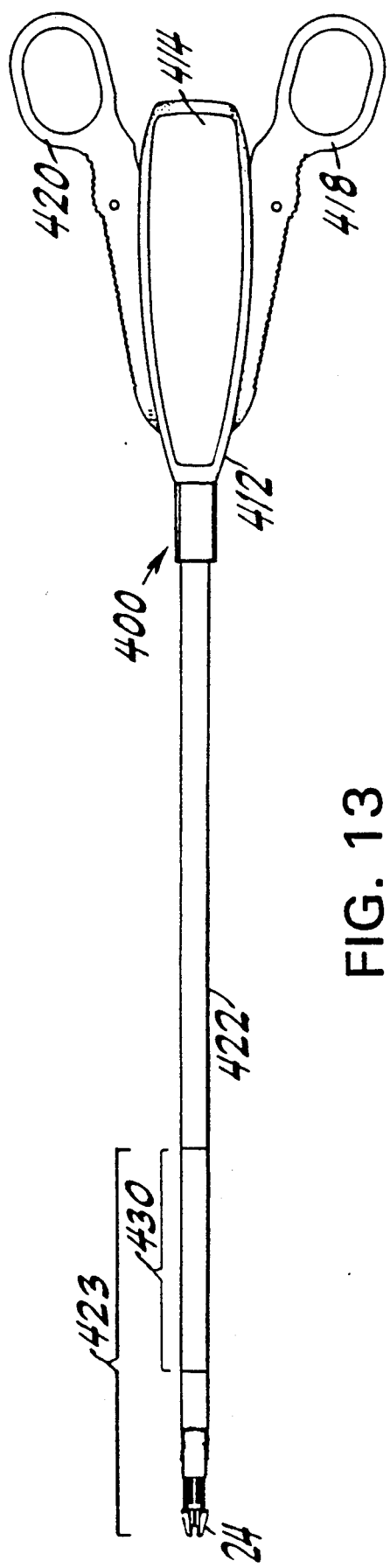
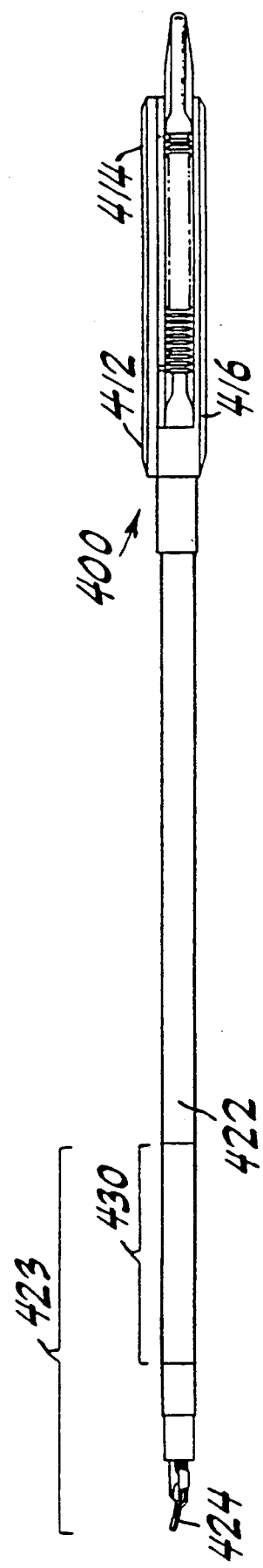
FIG. 13
FIG. 14

DRIVE MECHANISM FOR SURGICAL INSTRUMENTS

BACKGROUND OF THE INVENTION

1. Field of the Invention

This invention relates to surgical instruments and, more particularly, to instruments for applying surgical closure devices such as ligating clips and staples. Still more particularly, the invention relates to automatic surgical clip appliers and the means by which individual ligating clips are advanced to the clip-closing jaws at the distal end of the instrument.

2. Description of the Prior Art

Surgical ligating or hemostatic clips are used to ligate blood vessels, ducts or other tissue during surgery. The terms "ligating" and "hemostatic" are used interchangeably herein and, since these devices generally bind an object they will occasionally be termed "binding devices". The clips are generally U-shaped, have two parallel legs joined by an integral hinge portion and are applied with a clip applying forceps-type instrument used to crimp the clip legs together about the tissue to be ligated. When first introduced many years ago, each clip had to be applied individually by placing it in the jaws of a so-called "manual" clip applying, forceps-type instrument, and squeezing the jaws together. The clips for use with manual appliers are stored in a separate clip cartridge or dispenser from which the clips are retrieved one at a time. While manual appliers are still used, subsequent instruments were "automatic" clip appliers (some of them disposable) and incorporated a clip dispenser as part of the clip applying instrument. These improvements in clip appliers made these devices automatic in the sense of being able to automatically feed clips sequentially into the jaws. The automatic instruments generally include a pair of jaws for receiving, holding and crimping a single clip at a time and a feeding means for feeding a clip from the dispenser to the jaws. The jaws and feeder are activated in proper sequence by an activating means which usually includes a pistol-grip or pair of handles coupled mechanically to the feeder and jaws. The sequencing cycle may be done in a variety of ways but, generally, after the jaws are closed to crimp one clip the jaws are opened and supplied with a new clip ready to be applied when the jaws are closed again. Since different surgical procedures require the use of varying numbers of ligating clips, the automatic appliers are pre-loaded with different numbers of clips and in varying sizes. See, for example, U.S. Pat. No. 4,712,549 (Peters et al.), assigned to the assignee of this invention. While beneficial in many respects, the automatic appliers detract from the "feel" of manual appliers.

The simplicity of manual surgical clip appliers enables them to provide the surgeon with immediate tactile feedback because the "feel" of the clip being applied to the vessel is immediately transmitted from the distal, jaw end of the clip applier to the proximal, handle end. There is a direct connection between the two ends and any motion (i.e. squeezing) of the handle which is immediately transmitted to a corresponding motion of the jaws.

Automatic appliers, however, have always used a portion of the jaw closing mechanism to actually feed or move the clip from its storage cartridge or dispenser to the jaws. Sometimes, this is done by having the handles compress a spring during one portion of the cycle, the energy of the spring then being used in another portion of the cycle to feed a clip. In other instances, the handles move a feeder member in one portion of the cycle to push a clip into the jaws. The extra handle motion required to feed a clip rather than crimp it makes automatic appliers feel different to the user.

With the recent interest in endoscopic surgical procedures, surgical clip appliers have been adapted for endoscopic use by, among other things, somewhat disassociating clip-feeding from clip-crimping. This enhances security by enabling a surgeon during an endoscopic procedure to insert a clip applier into a cannula and place a clip between the jaws only when desired. Thus, in some prior art automatic clip appliers, the means by which a clip is fed to the jaws is independently triggered by actuation of a trigger mechanism while separate actuation of a jaw closing mechanism (for example, by squeezing a handle) actually closes the clip. However, even in these devices the movement of the jaw closing mechanism is linked to the clip feeding mechanism so that the user still does not get a true "feel" when the jaws are closed.

For example, U.S. Pat. No. 5,084,057 (Green et al.) discloses an apparatus and method for applying surgical clips in laparoscopic or endoscopic procedures. The device has a pistol grip actuating mechanism for closing the jaws and feeding the clip to the jaws. While the clip advancing mechanism is prepared for feeding a clip to the jaws, the actual feeding of the clip is interrupted by a trigger interposed between the feeding mechanism and the actuating mechanism so that clips will only be fed when the trigger is activated—not automatically as in other automatic clip appliers.

Another instrument which separates clip-feeding from clip-crimping is disclosed in U.S. Pat. No. 5,112,343 (Thórnton), assigned to the assignee hereof. This applier has pair of handles which are squeezed to compress a spring which is then released by a trigger to feed the clip. The releasing mechanism includes a trigger to move a resilient pawl out of engagement with a locking surface.

U.S. Pat. No. 4,662,373 (Montgomery et al.) discloses another example in the form of a surgical ligating instrument having a first activating means (e.g. a trigger) for activating a clip injector to push a clip into the jaws and a second activating means (e.g. a handle) for closing the jaws to crimp the clip. While first and second activating means are primarily independent they are interconnected mechanically such that actuation of the handle to crimp the clip does move other components in order to enable the clip injecting mechanism to be reset. The very nature of this interaction between the first and second activating mechanisms is sufficient to compromise the "feel" of the handle actuating mechanism.

It is an object of this invention to produce an automatic surgical clip applier which approximates the "feel" of a manual clip applier.

It is yet another object of this invention to produce an automatic surgical clip applier having one actuating mechanism for feeding the clip into the jaws of the applier and a second actuating mechanism for closing the jaws, the first and second actuating mechanisms being substantially mechanically independent of each other. It is another object of this invention to produce an automatic surgical clip applier wherein the means by which a clip is fed into the jaws of the applier works with a substantially constant feeding force with respect to each clip stored in the applier.

An additional object of this invention is to produce a surgical clip applier having a stored energy mechanism that is preloaded with and stores enough energy to feed all the clips in the entire cartridge.

It is yet another object of this invention to produce a surgical instrument having a self-contained energy source which can be used to physically move a desired component of the instrument.

It is also an object of this invention to provide a clip applier having a self-contained power source for feeding clips to the applier jaws which source is located along with the clips at the distal tip of the instrument. This arrangement facilitates simplification of the proximal handle end of the instrument and is adaptable to an instrument having a reusable handle end and a disposable or interchangeable distal tip containing the clips, jaws and power source.

SUMMARY OF THE INVENTION

These and other objects of the invention are achieved by the preferred embodiment disclosed herein. While the disclosure is centered around an automatic surgical clip applying instrument, it will be understood that the principles of the invention could be applied to surgical staplers or other instruments.

The invention disclosed herein is an improvement in a surgical instrument for applying a binding device such as a ligating clip to a surgical work site. The instrument is provided with a cartridge for storing a plurality of binding devices, a jaw means for receiving a binding device, a means for feeding the binding devices to the jaw means and a handle for actuating the instrument by applying the binding device to a selected area at the work site. The instrument is further provided with a self-contained power source having a power output, a feeder member for engaging at least one of the binding devices and for moving it into a position to be acted on by the applying means, a drive link operatively connecting the power source and the feeder member for transmitting power from the power source to the feeder member, and means associated with the applying means for enabling the power source to apply power to the drive link at a predetermined time.

Additionally the invention comprises the method of feeding surgical ligating devices from a storage means to an applying means. The method comprises the step of providing the instrument with a self-contained energized power source which has a power output preloaded with enough power to feed all the devices in the storage means. In a further step, the power output is connected to a feeder member for feeding the device to the working tip of the instrument so it may be applied.

DESCRIPTION OF THE DRAWINGS

FIG. 1 is a plan view of an endoscopic hemostatic clip applier constructed in accordance with the principles of this invention.

FIG. 2 is a side elevational view of FIG. 1.

FIGS. 3a, 3b and 3c are an exploded perspective views of the endoscopic hemostatic clip applier of FIG. 1.

(FIG. 4 being upside down relative to FIG. 3 and omitting spring 41).

FIG. 9 is a plan view of an applier constructed in accordance with the principles of an alternate embodiment of the invention.

FIG. 10 is a side elevational view of FIG. 9.

FIG. 12 is a perspective view similar to FIG. 4 but showing the features of FIG. 4 as they are adapted to the alternate embodiment of the applier of FIG. 9.

FIG. 12a is a diagrammatic representation of a portion of FIG. 10 taken along the line 12a-12a.

FIG. 13 is a plan view of an endoscopic hemostatic clip applier constructed in accordance with the principles of an alternate embodiment of the invention.

DESCRIPTION OF THE PREFERRED EMBODIMENT

Figure 3A:
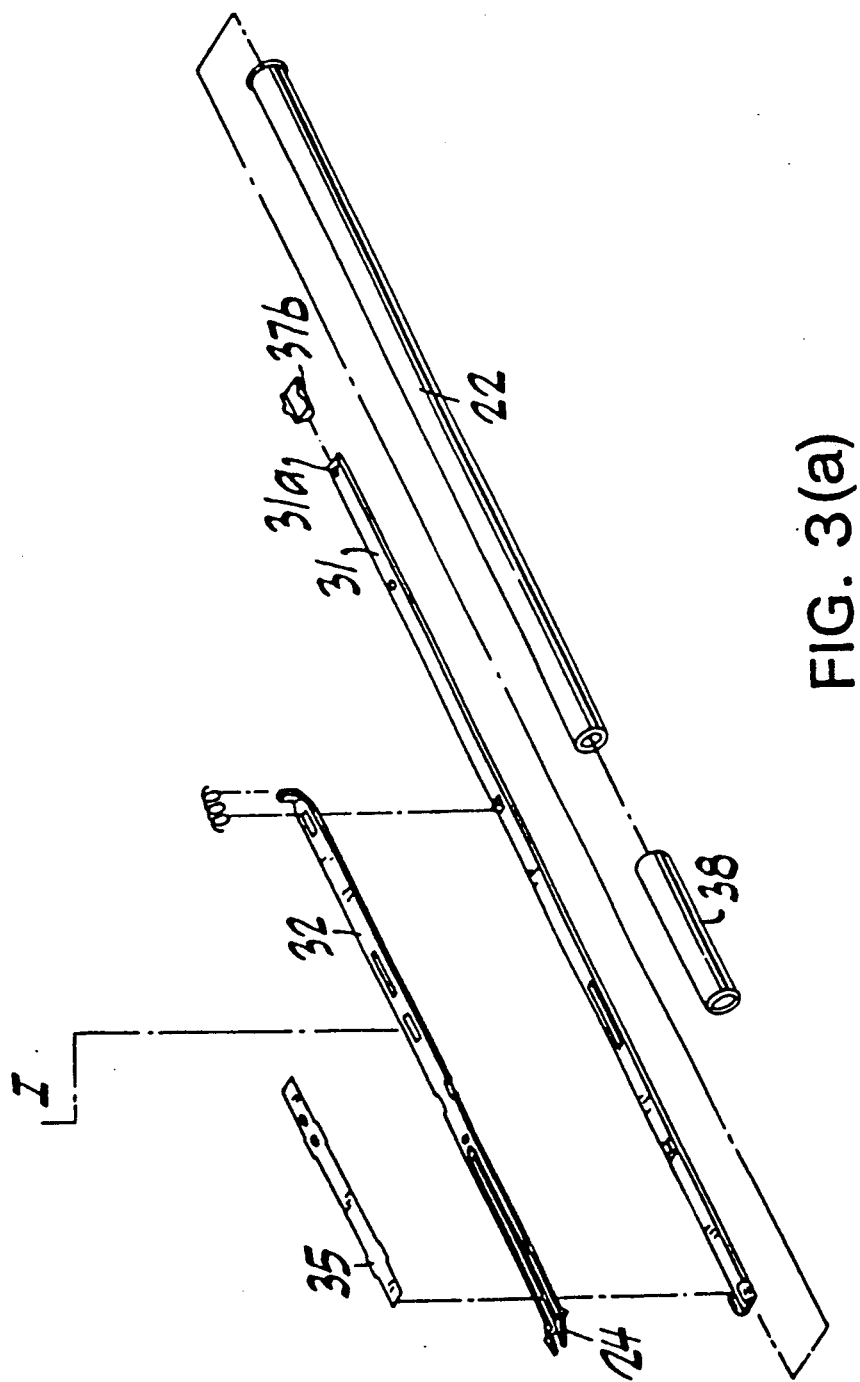
Figure 3B:
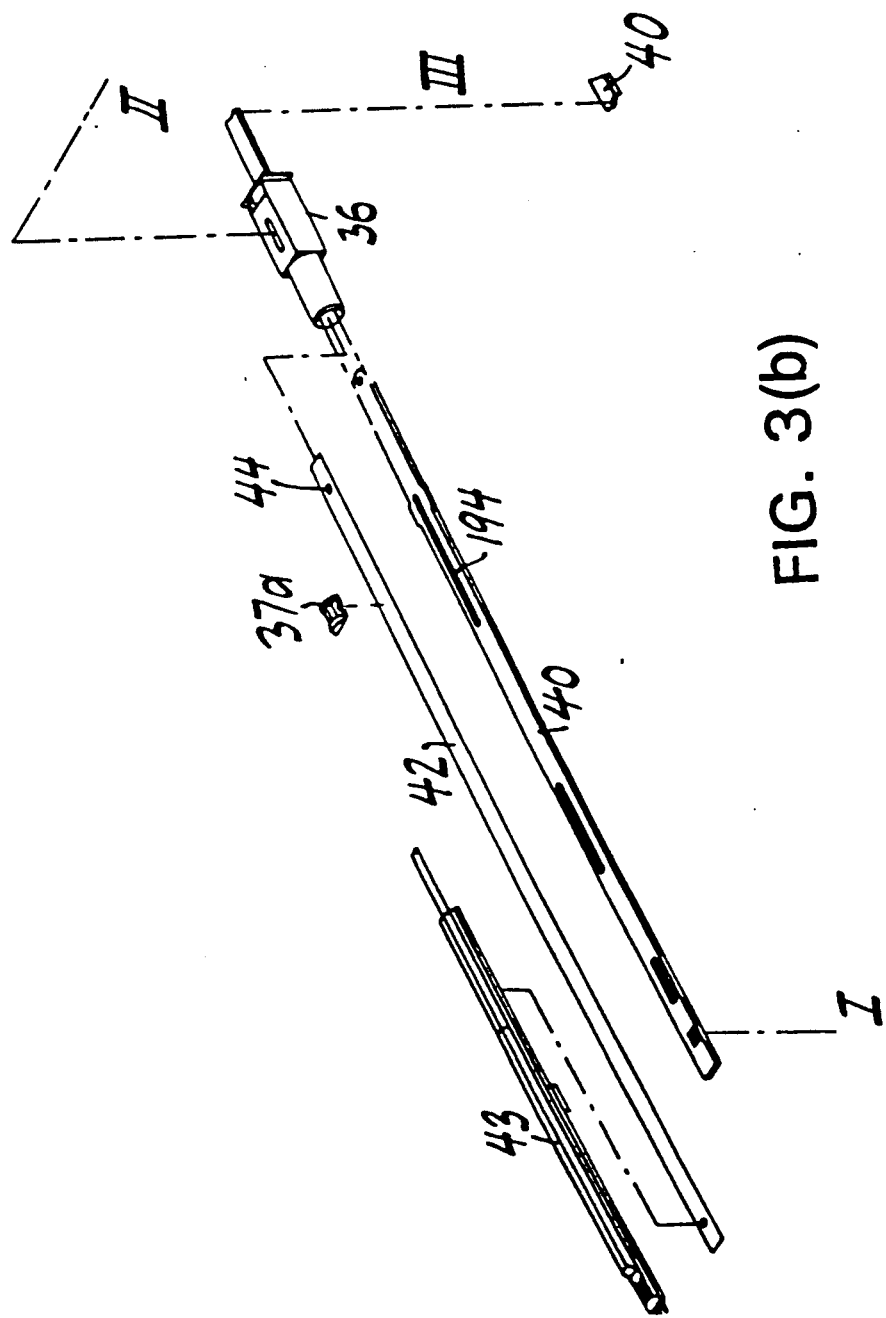

The present invention is embodied in an endoscopic instrument such as an automatic clip applier designated generally as 10 shown in plan and side elevational views in FIGS. 1 and 2 and in an exploded perspective view in FIGS. 3 and 3a. While the preferred embodiment disclosed herein is shown as an endoscopic clip applying instrument, it will be understood by those skilled in the art that the instrument could easily be used for open surgical procedures as well as for applications other than applying clips. It will also be understood that the invention could be adapted to a variety of endoscopic instruments such as staplers, etc.

Applier 10 comprises a housing 12 having top and bottom portions 14 and 16, respectively, a pair of ring handles 18 and 20 pivotally attached to housing 12 and a tubular extension portion 22 having a working portion 24 in the form of jaws at its distal end. Ring handles 18 and 20 are coupled to housing 12 via pivot pins 25 and 26 and by a pair of link members 28 and 29. One, distal end of each link member 28, 29 is coupled to the medial portion of its corresponding ring handle by a pivot pins 28a, 29a, respectively, situated distally of the ring portions 18a and 20a of handles 18 and 20. The other, proximal end of each link member 28 and 29 is coupled via a pivot pin 30 and retainer 30a to the proximal end of an actuating member 40. Member 40 extends distally from housing 12 within the tubular extension portion 22 and enables the transfer of power from the handles to the jaws 24 of the instrument. In the preferred embodiment, instrument 10 is a clip applier and the working portion is similar to that described in U.S. Pat. No. 5,112,343 (Thornton), assigned to the assignee hereof and incorporated herein by reference. One difference is that drive link 33 in the device of the '343 patent is used to both feed clips and transfer power to the jaws. In the present embodiment, however, these functions are separated and actuating member 40 is used to close the jaws while a separate feeder member 42 is used to feed the clips, as will be understood below. Member 40 extends through compression spring 41 which, as will be understood below, is used only to bias handles 18 and 20 open. In the applier described in the '343 patent, the compression spring was used to both bias the handles and feed the clips.

Extending distally from housing 12 within cylindrical tube 22 are the working components of the applier which enable it to operate as intended, these components comprise closure member 31 (connected via hole 31a to pin 31b in housing 12), jaw member 32, actuating member 40, feeder member 42, clip storage/dispensing cartridge 43 and jaw stabilizer 35. Gasket/spacer inserts 37a and 37b are interposed between the interior of cylindrical tube 22 and the closure member 31, actuating member 40 and feeder member 42 in order to support these components and provide an additional seal against escape of gases utilized during the endoscopic procedures. Additional gaskets (not shown) may be used in other portions of applier 10 to provide additional seals and a front end tapered tip component 38 may be used to secure the distal tip of the various components and provide a smooth transition to facilitate insertion of applier 10 into a cannula. Closure member 31, actuating member 40 and feeder member 42 pass from the interior of housing 12 to the exterior through longitudinal track 60 (described below) and adapter 36.

Actuating member 40, feeding member 42 and clip cartridge 43 cooperate with other components at jaws 24 as more clearly described in the aforementioned U.S. Pat. No. 5,112,343 to feed clips to the jaws. The proximal end of feeding member 42 is provided with an aperture 44 which enables it to be connected to the output of power subassembly 100 as will be described below. Power subassembly 100 is attached to the interior side of housing portion 14 and comprises a self-contained energy source able to be used in a variety of applications. In the preferred embodiment, subassembly 100 is used in a ligating clip applier to feed clips from a clip storage cartridge to a clip-closing jaw assembly which is activated by actuating member 40. Unlike the prior art device described in the aforementioned U.S. Pat. No. 5,112,343 in which the clip feeding and jaw closing functions of the applier are activated, controlled and powered by the motion of the handles, subassembly 100 provides the power to feed clips from the clip cartridge 43 to the jaws 24 while the actual closure of the jaws is caused by handles 18 and 20. Consequently, the "feel" of the instrument is more like that of a manual applier.

Figure 4:
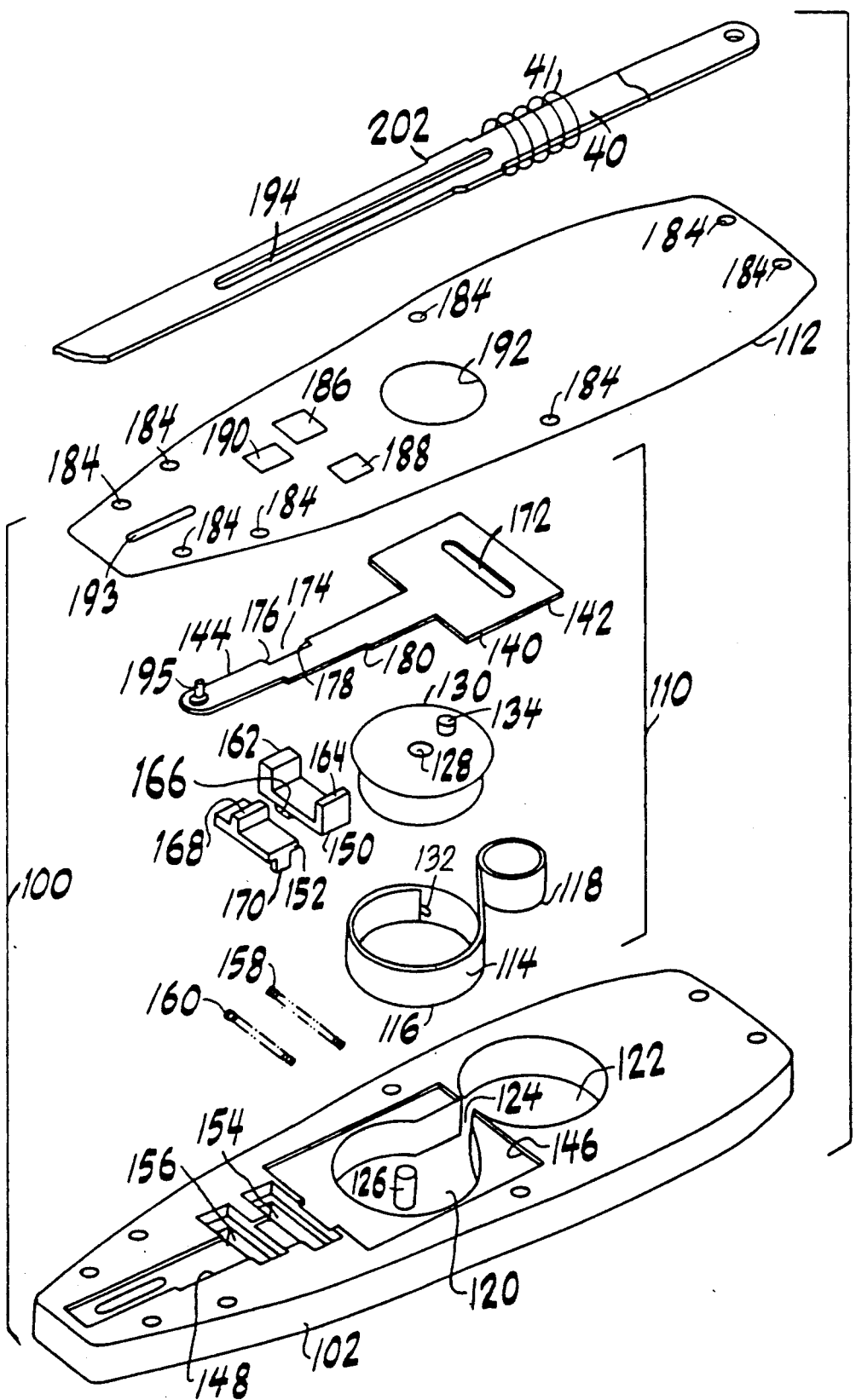
FIG. 4 is an exploded view of the power subassembly portion of the housing of the applier shown in FIG. 3.
Figure 5:
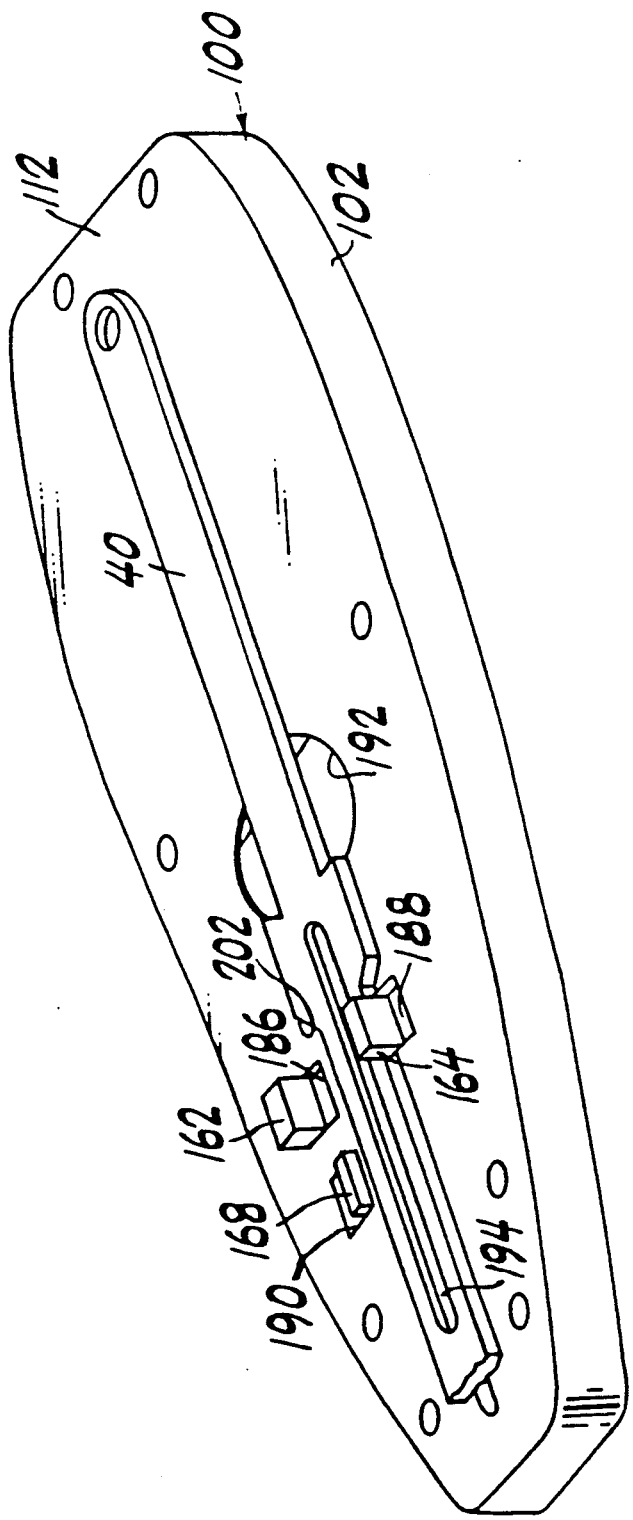
FIG. 5 is a perspective view of the components of FIG. 4 shown in an assembled configuration.

As shown in FIGS. 3, 4 and 5, subassembly 100 forms a part of the housing 12 of the instrument and the shape of subassembly 100 may be changed to accommodate the shape of the desired housing. Subassembly 100 lies under housing portion 14 as viewed in FIG. 3 and the views shown in FIGS. 4 and 5 are inverted from FIG. 3. Subassembly 100 comprises subassembly body 102, constant-torque spring drive assembly 110 and retention cover 112. Body 102 is provided with a plurality of uniquely shaped recesses 120 and 122 to accommodate various portions of constant force drive assembly 110. Constant-torque spring 114 is a conventional structure formed of a drive coil 116 and a take-up coil 118 which are co-planar and fit into recesses 120 and 122, respectively. Passage 124 accommodates the passage of the coil spring from drive recess 120 to take-up recess 122, the former being provided with a central post 126 which receives aperture 128 of spool 130. Hook 132 is secured to the inner end of the coil spring within drive coil 116 and is attached to spool 130 in a conventional manner. Spool 130 is provided with a perpendicularly extending drive post 134 which provides the rotational output of the subassembly as will be understood below. Drive assembly 110 is preloaded with enough energy to feed all of the clips in cartridge 43 and the energy used to feed each clip is constant from the first clip to the last.

Body 102 is provided with additional recesses to accommodate various other components of drive assembly 110 which regulate and transmit its power output. Drive link member 140, having a proximal head end 142 and a distal extension 144, is planar and is slidingly received within contiguous rectangular recesses 146 and 148 in body 102. Control latch members 150 and 152 are slidingly received in recesses 154 and 156, respectively. Also received in recesses 154 and 156 are biasing springs 158 and 160, respectively. Latch 150 has upwardly extending tabs 162 and 164 and downwardly extending spring tab 166. Latch 152 has an upwardly extending tab 168 and a downwardly extending spring tab 170. The springs and spring tabs are arranged to bias latches 150 and 152 in opposite transverse directions as will be understood below.

Drive member 140 overlies spool 130 and latches 150 and 152 such that post 134 extends through transverse slot 172 and the latch tabs extend upwardly past the distal extension 144. The extension is provided with various notches and edges which serve to coordinate the rotary motion of post 134 with other components. Notch 174 has distal and proximal edges 176, 178 which interact with tab 168 on latch 152 at different parts of the operating cycle. Edge 180 on the other side of extension 144 interacts with tab 164 of latch 150. The head end 142 of drive member 140 and extension 144 reciprocate longitudinally in rectangular recesses 146 and 148, respectively, the recesses being as deep as the thickness of drive member 140. Cover 112 overlies drive member 140 and retains all components while enabling their motions within body 102. Cover 112 is provided with a plurality of peripherally arranged attachment points 184, for attaching the cover to corresponding points on body 102, and a plurality of apertures to expose the latch tabs and spool post. Apertures 186 and 188 permit latch tabs 162 and 164 to protrude above the surface of cover 112 and aperture 190 does the same for tab 168. Aperture 192 provides clearance for spool post 134 and access to the post during assembly. Slot 193 in cover 112 is aligned with slot 194 in actuating member 40, slot 194 serving as a relief slot to receive the tip of pin 195 which connects hole 44 of feeder member 42 to the distal tip of drive member extension 144. Actuating member 40 and feeder member 42 are parallel and each moves at a different time in the cycle of operation. It will be understood that for clarity FIG. 5 is not drawn to scale and that spring 41 and feeder member 42 are omitted. Actuating member 41 is normally spaced above cover 112 to allow clearance for spring 41.

The instrument shown in FIGS. 3, 4 and 5 is considered a fully automatic instrument because the clip feeding and jaw closing functions of the applier are totally controlled by movement of handles 18 and 20. A slightly modified version of this instrument will be described below with reference to FIGS. 9 through 12 which disclose a semi-automatic clip applier in which the clip feeding function is interrupted by the necessity for a user to actively trigger the feeding of a clip into the jaws.

Figure 6:
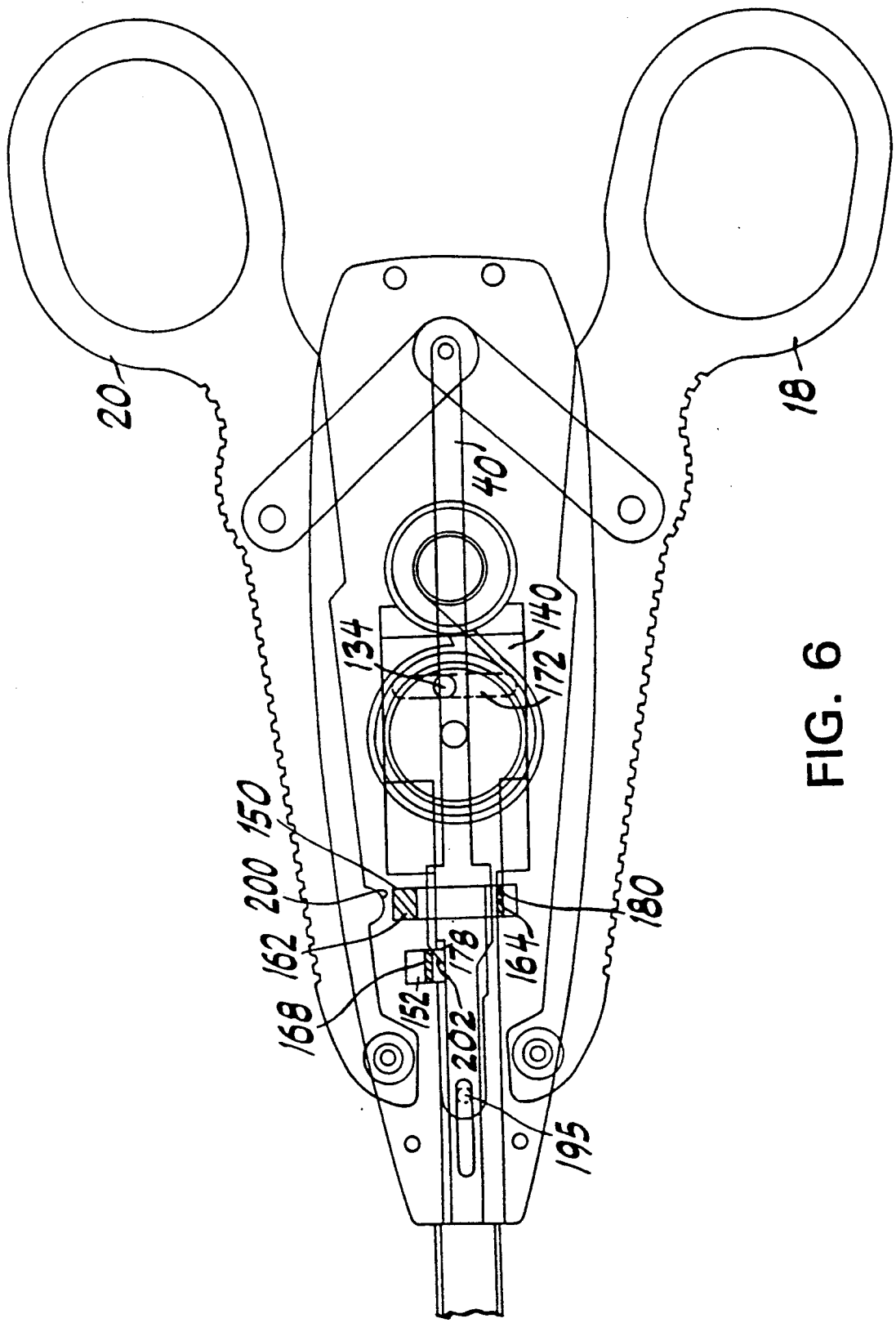
FIGS. 6, 7 and 8 are sequential views of the positions of components of the applier of FIG. 1 at various points during the operating cycle of the applier.
Figure 7:
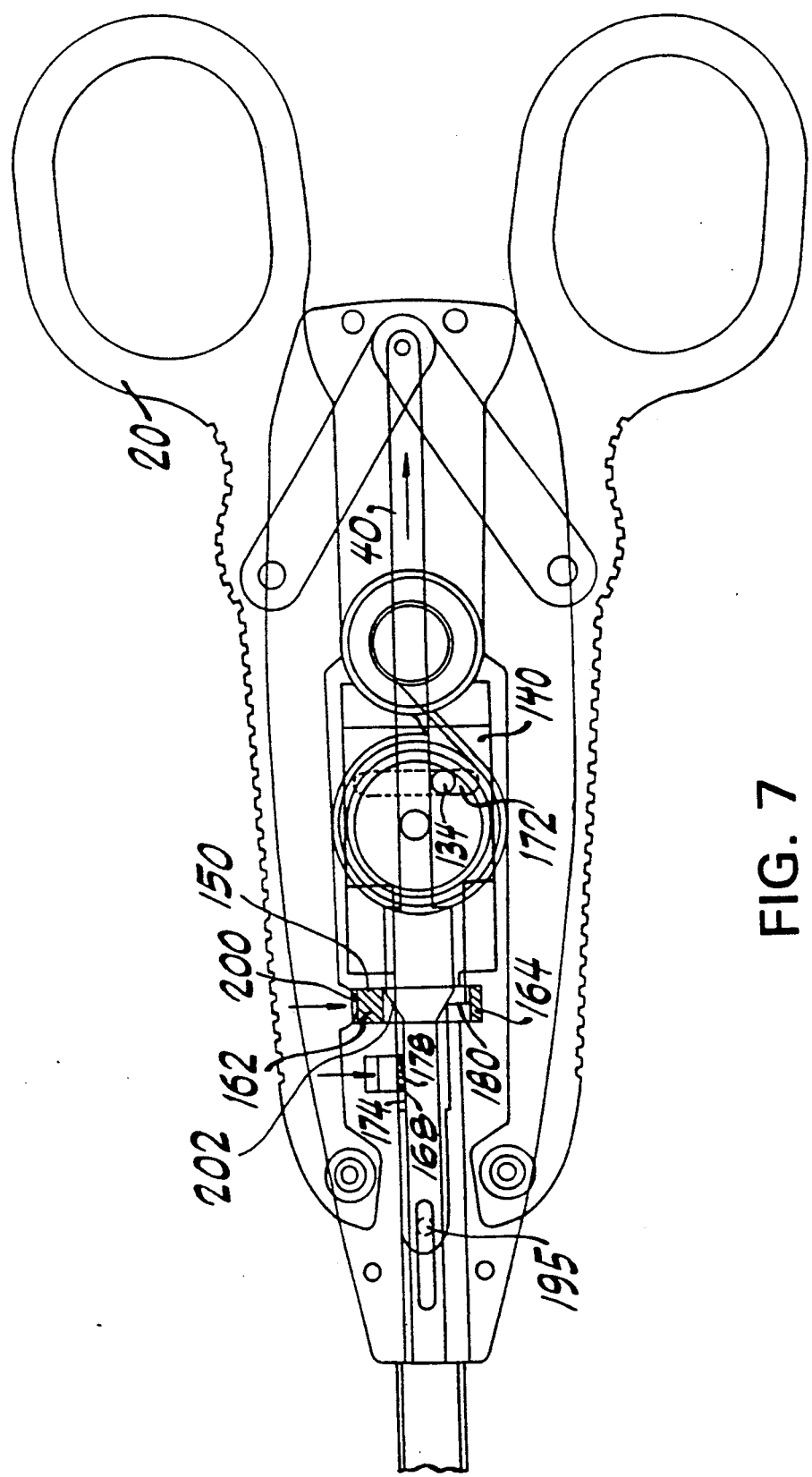
Figure 8:
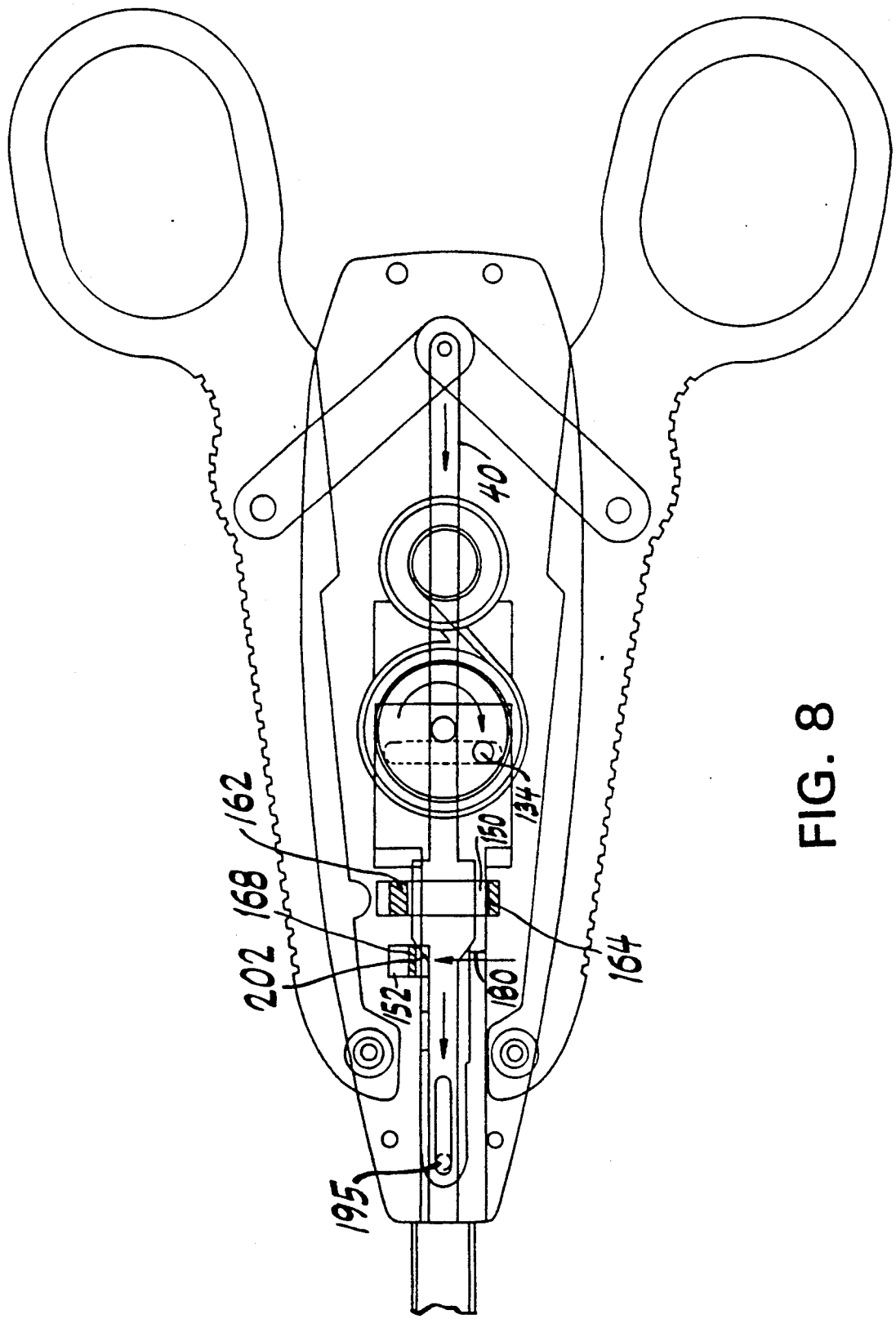

Referring now to FIGS. 6, 7 and 8, the cyclical operation of the applier and power subassembly will be described as they relate to the operation of automatic clip applier 10. In these Figures it will be understood that actuating member 40 reciprocates longitudinally in response to the motion of handles 18 and 20 and feeder member 42 is used to transmit power from subassembly 110 to the distal working tip. Latches 150 and 152 interact with edges formed in the side of actuating member 40 to trigger and control the power subassembly at appropriate times in the operating cycle of instrument 10.

At the beginning of the cycle, the handles are open as shown in FIG. 6 and tab 164 of latch 150 is abutted against edge 180. As best seen in FIG. 7, protrusion 200 on the inward side of handle 20 presses against the laterally outer surface of tab 162 of latch 150 in order to move it laterally to disengage the abutment between edge 180 and tab 164 to release the drive member to move distally under the influence of spool post 134. As the handles are squeezed from the position of FIG. 6 to that of FIG. 7, actuating member 40 is moved proximally. In conventional automatic appliers the action of squeezing the handles is also used to move other components associated with advancing the clip to the jaws. This requires the handles be closed somewhat before any closing of the jaws is observed. In the subject invention, on the other hand, the closure of the handles will immediately be observed in the closure of the jaws because of the direct connection between the jaws (via member 40) and the handles. This results in much less squeezing motion of the handles being required to close the jaws at the very end of the cycle and produces an automatic clip applier more closely approximating the feel of a manual applier.

Ramp surface 202, which had been restraining tab 168 from laterally inward motion (urged by its spring 160) as best seen in FIG. 6, is thereby moved proximally to release tab 168 and permit it to seat in notch 174. Simultaneously, the drive member moves distally under the influence of spring 114 until edge 178 abuts tab 168 of latch 152. This position of the components cocks the power subassembly to be ready for actuation once tab 168 is moved laterally out of engagement with edge 178 during a later portion of the cycle. Meanwhile, continued squeezing of the handles causes the jaws to close in a conventional manner thereby crimping a clip between the jaws.

As shown in FIG. 8, as the handles are released at the end of the cycle, tab 162 of latch 150 stays laterally spaced from any interference with actuating member 40 because of the bias of spring 158. Actuating member 40 moves distally a sufficient distance so that ramp 202 pushes tab 168 laterally to disengage tab 168 from edge 178 thereby releasing drive member 140 and allowing it to complete its cycle. Drive member 140 moves distally, thereby pushing pin 195 attached to feeder member 42 to its distal-most position, and immediately thereafter moves proximally, because of the continuing rotation of post 134, to the position shown in FIG. 6 at which point tab 164, continuously biased against the side of actuating member 40 by spring 158, clears edge 180 and moves into a locking position which stops post 134 from further rotation. This results in a clip being placed in position between the jaws, ready to be crimped.

An additional advantage of the constant force feed mechanism is that as spool 130 rotates, post 134 moves from a zero velocity at one extreme position (on the axis of the applier) through a maximum velocity when the peg is at 90° relative to its starting position to a zero velocity at the diametrically opposed position (again on the axis) which coincides with the clip being placed between the jaw members. Consequently, the clip is fed relatively gently to the jaws.

Tabs 162 and 164 of latch 150 are sufficiently spaced from each other so the latch does not frictionally engage actuating member 40 during its normal motion and only interacts with the handle protrusion 200 and with the drive member 140. The spacing of the tabs permits handle 20 to lock and release drive member 140 while allowing actuating member 40 to unobstructedly reciprocate between the tabs. (The enlarged portion of member 40 between tabs 162 and 164 serves to engage member 40 with spring 41). Latch 152, on the other hand, interacts with drive member 140 and slightly with actuating member 40. Neither latch 150 nor 152 detract from the direct connection between the handles and the jaw closing mechanism of applier 10. Essentially all of the energy applied to handles 18 and 20 is translated to jaw closure unlike in prior art devices where a significant portion of the energy is diverted to clip feeding.

As mentioned above, the invention is adaptable to a semi-automatic operation as well as to fully automatic operation. An embodiment of a semi-automatic clip applier 300 is shown in FIGS. 9 through 12. Those components of applier 300 which are identical to like components of applier 10 are numbered identically in these drawings.

Figure 11:
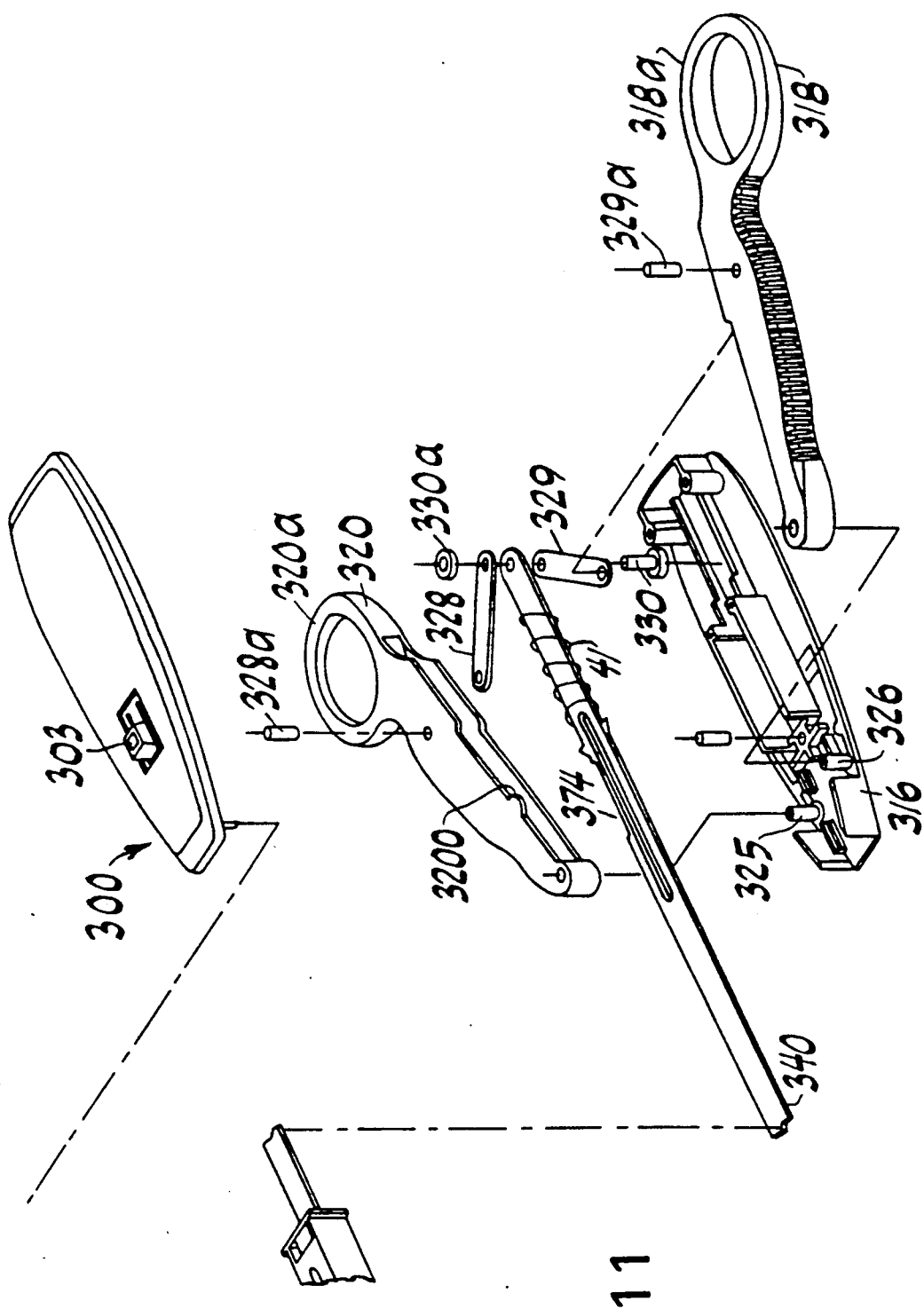
FIG. 11 is an exploded perspective view of the applier of FIG. 9.

Applier 300 has component parts that are numbered similarly to the component parts of applier 10 except that they are prefixed by the number "3". The primary difference between appliers 10 and 300 lies in the trigger 303, the shape of actuating member 340 and the replacement of tab 168 with an extended tab 368. Thus, the components shown in FIG. 11 are, with the exception of trigger 303 and member 340, the same as those described with respect to FIG. 3 and need not be further described. Similarly, the components of FIG. 12 are, with the exception of tab 368 and member 340, the same as those described in FIG. 5. Trigger 303 is cantilevered and has a bottom sloping surface like the trigger disclosed in the aforementioned U.S. Pat. No. 5,112,343. As shown diagrammatically in FIG. 12a, tab 368 extends above cover plate 312 far enough to lie in the path of the bottom sloping surface of trigger 303 when it is depressed. Actuating member 340 has an elongated notch 374 in order to enable actuating member 340 to reciprocate longitudinally without affecting tab 368 which is continuously biased laterally by its spring into locking engagement with drive member 140 (not shown). The sloped surface on the bottom of trigger 303 functions similarly to slope 202 of applier 10 and pushes tab 368 laterally to overcome this spring bias and momentarily allow the drive member to complete its cycle. Releasing pressure on trigger 303 permits tab 368 to move laterally into notch 178 (best seen in FIG. 6) of the drive member the next time the notch is adjacent the tab.

The invention is adaptable to other embodiments in which the power subassembly may operate in a rotary motion that is aligned with the axis of the instrument rather than transverse to the axis as shown in the preceding embodiments. This type of variation would make the invention adaptable to tubular shaped portions of the instrument and as such would make the invention adaptable to being situated in distal portions of endoscopic instruments (which tend to be cylindrical) rather than in proximal portions of endoscopic instruments (which tend to be more rectilinear). Such an embodiment would make the invention particularly suitable for endoscopic clip appliers having removable and/or disposable distal tips which are operable with a common and/or reusable body portion. Such an embodiment of the invention is disclosed in FIGS. 13-20.

Figure 14A:
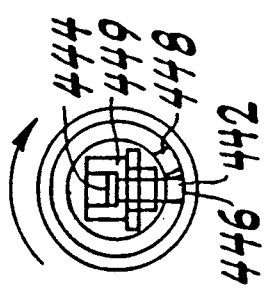
FIGS. 14a and b are end and cross-sectional side elevational views of the power subassembly portion of the applier of FIG. 13.
Figure 14B:
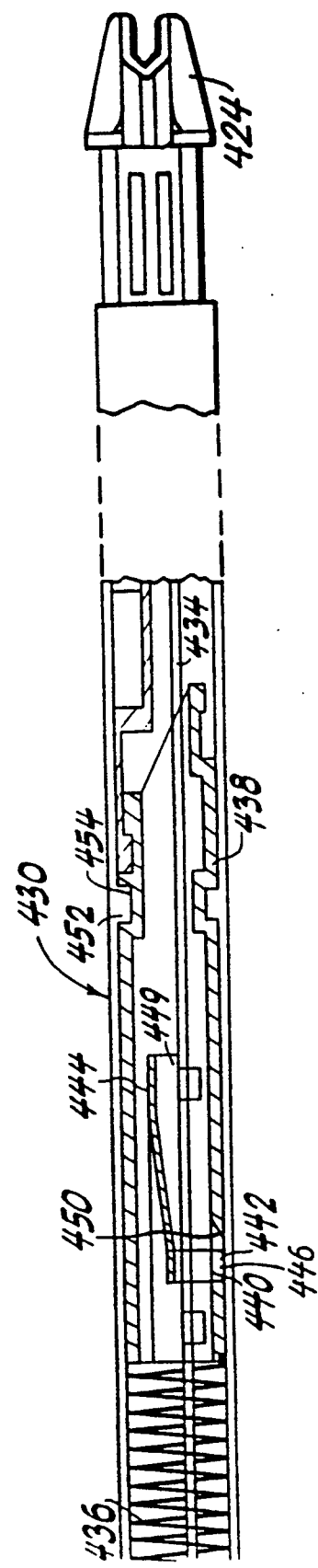
FIG. 14 is a side elevational view of FIG. 13.

Referring now to FIGS. 13 and 14, there is shown a plan and elevational view of an embodiment of an endoscopic clip applier 400 having a proximal housing 412 comprising top and bottom body portions 414 and 416 and a pair of pivotably movable handles 418 and 420. Applier 400 has a tubular extension 422 extending distally from housing 412 and the distal tip of tubular portion 422 is provided with a disposable or removable working tip portion 423 having distal working members 424. While the embodiment of the invention disclosed herein is a hemostatic clip applier, it will be understood that the invention may be adaptable to other applications.

Removable tip portion 423 is operatively and detachably secured to the distal end of tubular portion 422 by means not shown. Tip portion 423 includes a power subassembly 430 which is more particularly described by reference to FIGS. 14 through 20 which show a cross-sectional elevational view of power subassembly 430 in various stages of its operation.

Referring now to FIG. 14, it will be understood that power subassembly 430 is a section of tip portion 423 which is interposed between tubular extension 422 and working members 424. Power subassembly 430 comprises a proximal end 432 detachably connected (by means not shown) to tubular extension 422. Subassembly 430 also includes working members 424 at the tip of the instrument and is disposable or removable as a unit with the tip. The interconnection between the working components of power subassembly 430 and tip 424 is omitted for clarity.

Power subassembly 430 includes a closure base bar 434 which extends from proximal end 432 distally to some operative connection with working members 424. In the case of a clip applier closure base bar 434 is analogous to actuating member 40 of applier 10 discussed above. It will be understood that bar 434 may be merely a distal extension of an actuating member which is linked to handles at the proximal end of the instrument and, since the feeding and sequencing functions of applier 400 are situated at the distal tip of the instrument, the connection between the handles of applier 400 and the actuating member may be very straightforward.

Power subassembly 430 comprises several components which are arranged in a cylindrical manner around closure base bar 434 and which perform similar functions to power subassembly 100. The primary difference between power subassembly 100 and power subassembly 430 is that the latter has an axis of spring rotation which is parallel to the axis of the tubular extension 422 while the former has a spring rotation axis which is perpendicular to the tubular extension 422. The latter provides a rotational output to the clip feeding mechanism while the former provides a linear output. Subassembly 430 comprises a torsion spring 436, a rotatable cylindrical body 438 (analogous to drive link member 140) and a stop mechanism 440. Spring 436 provides the rotational drive to body 438, the motion of which is controlled by stop mechanism 440 in order to sequence clip feeding into the jaws at the proper times of the cycle.

Stop mechanism 440 comprises a plunger 442 which is situated at the end of a cantilevered spring 444 which is radially outwardly biased in order to stop the rotation of body 438 at certain points of the cycle. Body 438 includes peripheral slots 446 and 448. Stop mechanism 440 is secured to and movable with a carrier body 449 attached to the closure base bar 434. As the handles of the applier are closed and closure base bar 434 moves distally, plunger 442 rides up the front ramp surface 450 of slot 446 and thereby releases body 438 permitting spring 436 to rotate it about the axis of the applier. Annular rib 452 on the interior surface of the body of subassembly 430 mates with annular groove 454 in body 438 in order to constrain body 438 to rotary motion only.

Figure 15A:
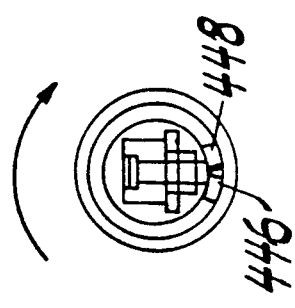
FIGS. 15a and b through 20a and b are sequential views of the positions of the components of the applier of FIG. 13 at various points during the operating cycle of the applier.
Figure 15B:
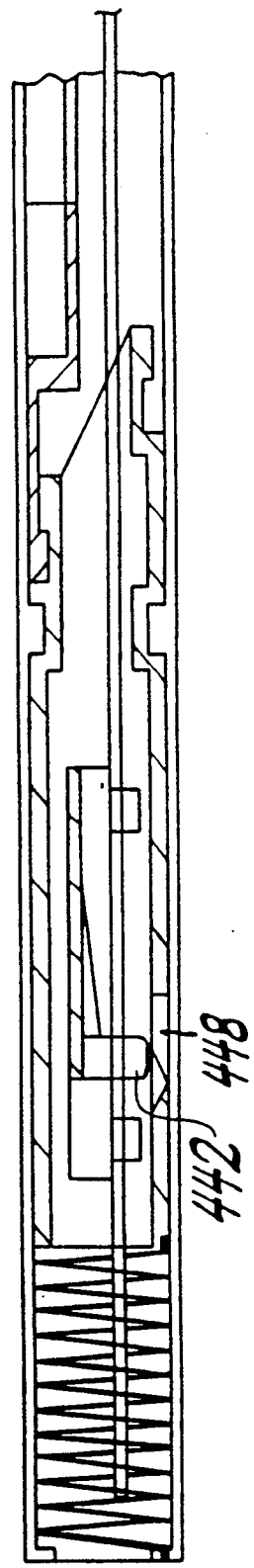
Figure 16A:
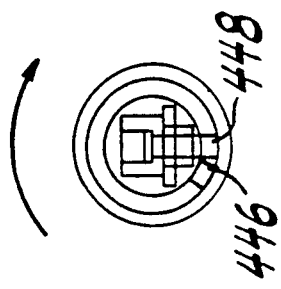
Figure 16B:
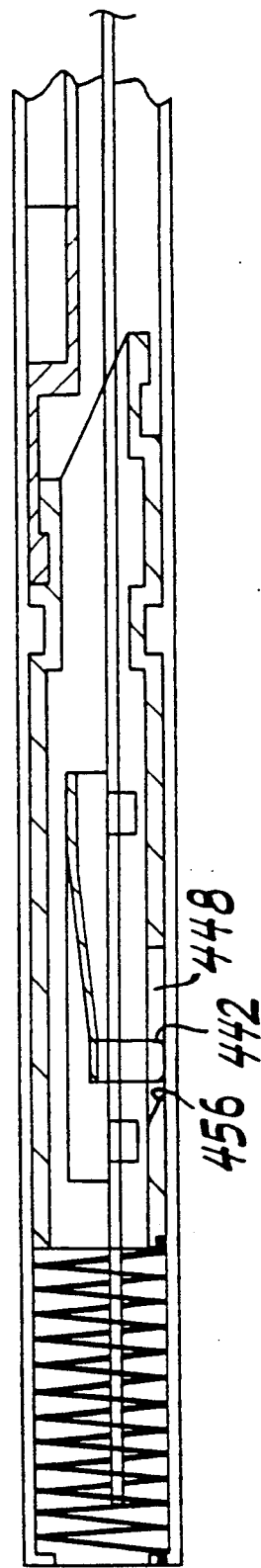
Figure 17A:
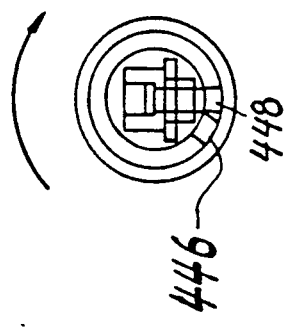
Figure 17B:
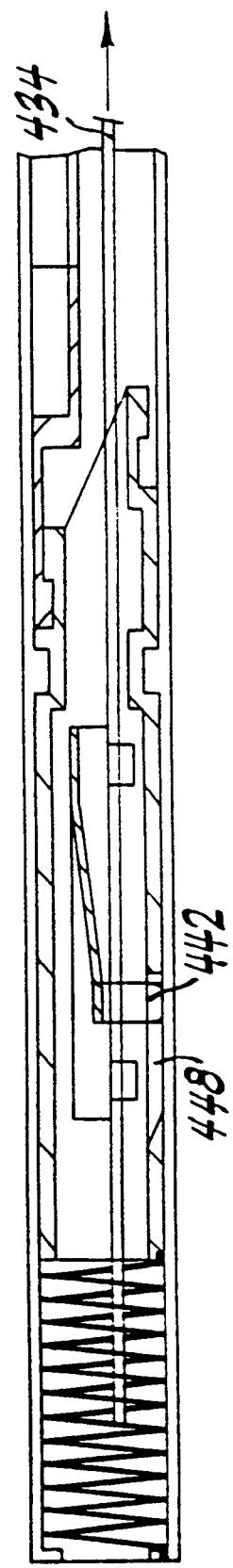

As shown in FIG. 15, when plunger 442 has been removed from slot 446 the body 438 immediately begins to rotate and, because of the proximity of slot 448 to slot 446, plunger 442 drops into slot 448 (as best seen in FIG. 16) which is provided with a rearwardly sloping surface 456. As shown in FIG. 17, slot 448 is elongated in order to enable further distal movement of clip closure base bar 434 to close the jaws of the clip applier while still preventing any further rotational motion of body 438.

Figure 18A:
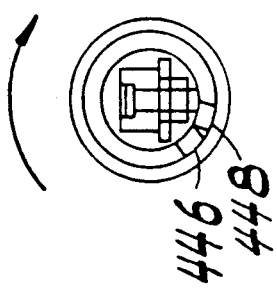
Figure 18B:
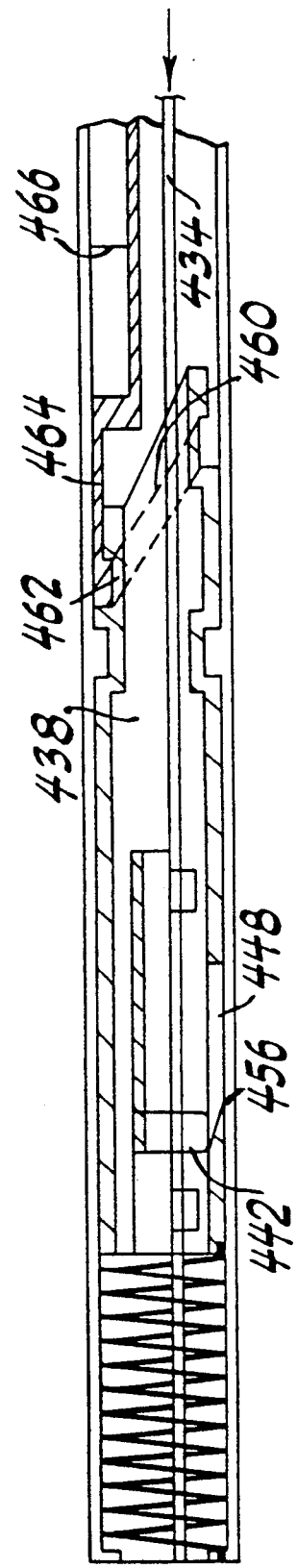
Figure 19A:
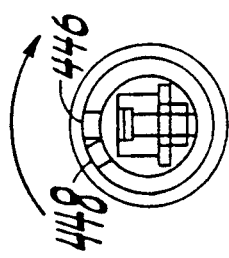
Figure 19B:
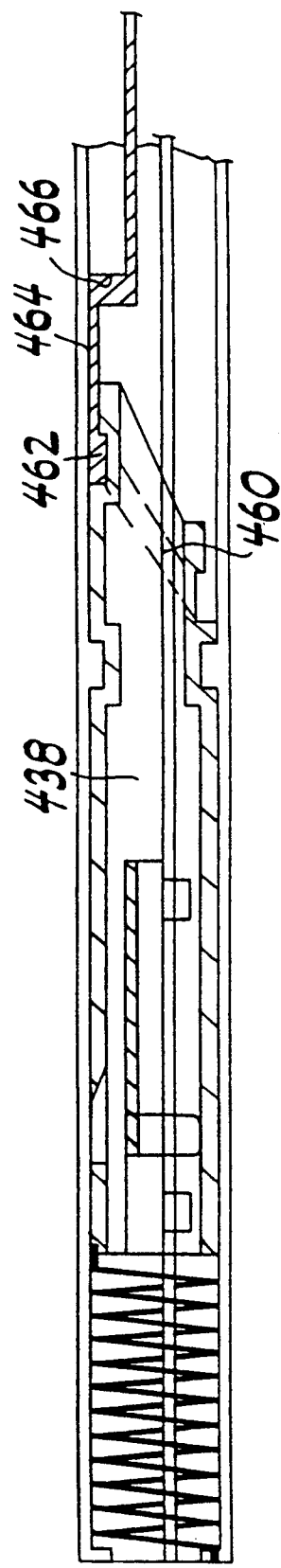
Figure 20A:
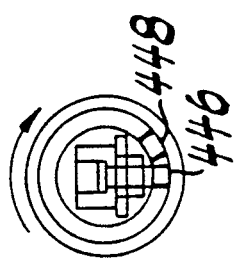
Figure 20B:
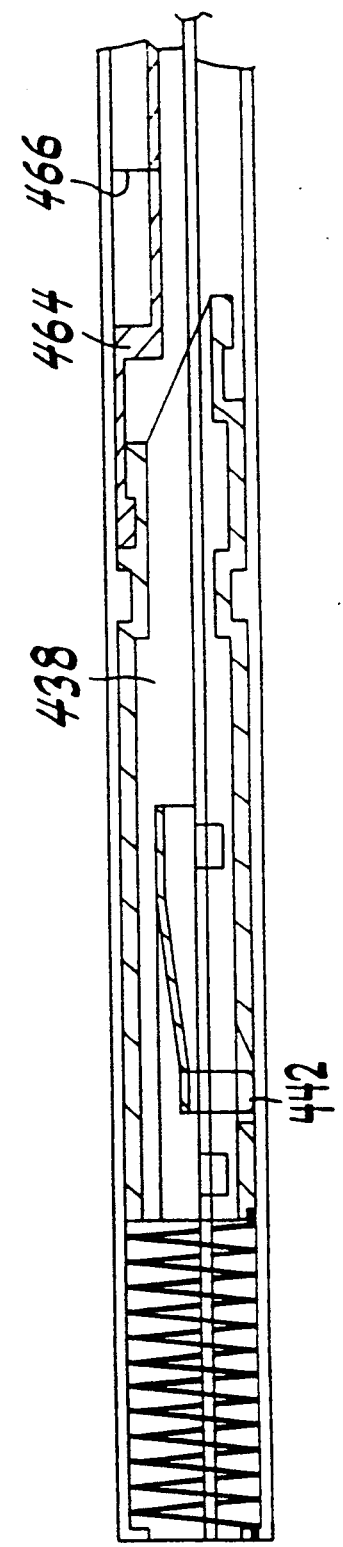

As the handles are opened at the end of the cycle, clip closure base bar 434 is moved proximally as shown in FIG. 18 thereby causing plunger 442 to ride up rear surface 456 of slot 448 thereby again permitting body 438 to rotate as shown in FIG. 19 until the plunger is again adjacent slot 446 at which time the rotary motion of body 438 is again stopped. During the cycle of operation shown in FIG. 19, body 438 rotates about its axis. The distal tip of body 438 is provided with an inclined annular slot 460 which is engaged with a clip feeder pin 462 provided at the proximal end of a feeder member 464. The latter is operatively connected with clip cartridge 466 in order to feed clips in a conventional manner to the jaws of the applier. It will be understood that as body 438 rotates through almost 360° feeder pin 462 is driven longitudinally to its distal-most position and immediately returned to its more proximal starting point as shown in FIG. 20.

In addition to the mechanically powered subassemblies disclosed herein, it will be obvious to those skilled in the art that the spring power mechanisms 110 and 436 may be replaced by any power source (e.g. $CO_2$ cartridge or other fluid, electrical, etc.) which can be adapted to provide comparable operating characteristics.

It will be understood by those skilled in the art that numerous other modifications and improvements may be made to the preferred embodiment of the invention disclosed herein without departing from the spirit and scope thereof.

What is claimed is:
1. A surgical instrument comprising:
  means for storing a plurality of binding devices;
  means for applying at least one of said binding devices to an object at a surgical work site;
  means for feeding said binding devices at least one at a time to said applying means, said means for feeding comprising:
  power source means having a power outer, said power source means being pre-loaded with sufficient energy to feed more than one said binding devices;

a feeder member means for engaging at least one of said binding devices and for moving it into a position to be acted on by said applying means;

a drive link means operatively connected to said power source means and said feeder member means for transmitting power from said power source means to said feeder member means; and means associated with said applying means for enabling said power source means to apply said power output to said drive link means at a predetermined time.

2. A surgical instrument according to claim 1 wherein said applying means comprises a pair of squeezable handles and said enabling means comprises a portion of one of said handles adapted to cooperate with said power source means.

3. A surgical instrument according to claim 1 wherein said power source means comprises a spring and said drive link means comprises a cylindrical body cyclically rotatable about its axis.

4. A surgical instrument according to claim 3 wherein said cylindrical body comprises:

an annular groove perpendicular to the axis of said body and adapted to engage an inwardly extending annular rib on a surface portion of said power source means adjacent thereto;

an annular cam groove inclined to the axis of said body and adapted to engage an inwardly extending cam connected to said feeder member means.

5. A surgical instrument according to claim 1 wherein said power source means comprises a flat, wound coil spring having a drive coil portion and a take-up portion and said drive link comprises a flat plate cyclically reciprocable in a predetermined direction.

6. A surgical instrument according to claim 5 further comprising a transversely extending post secured to one end of said spring and wherein said drive link comprises an aperture for mateable engagement with said post.

7. In a surgical instrument for applying a binding device to a surgical work site, the instrument having a cartridge for storing a plurality of said binding devices, a jaw means for receiving a binding device, a means for feeding the binding devices to said jaw means, a handle for actuating the instrument to apply the binding device to a selected area at the work site, the improvement comprising:

spring means having a drive coil and a take-up coil, each of said coils situated in a common plane;

a post extending perpendicularly to said plane for being rotated by the drive coil of said spring means;

a planar drive member situated in a plane parallel to said common plane and having a transverse slot for receiving said post therethrough, said drive member adapted to reciprocate longitudinally in response to rotary motion of said post;

means for connecting said drive member to said feeding means;

control means for enabling said drive member to move cyclically through a distal/proximal cycle at predetermined points relative to the position of the handles of the instrument.

8. In a surgical clip applier for applying ligating clips to a surgical work site, said applier comprising at least one clip for being applied to the surgical work site, a means for applying said clip to the surgical work site, and means for feeding a clip to said applying means, the improvement comprising:

a pre-loaded energy source; and connecting means for operatively connecting said energy source to said means for feeding, said pre-loaded energy source being initially pre-loaded with enough energy to feed more than one ligating clip to said means for feeding one at a time.

9. A method of feeding surgical binding devices from a storage means loaded with a plurality of said binding devices and attached to a surgical instrument to a binding-device-applying-means at the working tip of said surgical instrument comprising the steps of:

providing said surgical instrument with a self-contained, pre-loaded energized power source means which has a power output means and is loaded with sufficient power to feed more than of the binding devices stored in said storage means;

operatively connecting said power output means to a means for feeding said binding device to the working tip.

10. A method according to claim 9 further comprising the step of:

controlling the operation of said power source means in a cyclical manner to produce a power output therefrom only at predetermined points in the operation of said instrument.

11. A method according to claim 10 further comprising the step of:

cocking said power source means in response to a predetermined position of said binding device applying means such that a change of said position then results in said production of a power output from said power source means.

12. A method according to claim 9 further comprising the step of:

providing a cylindrical drive link to transmit power from said power source means to said feeding means.

13. A method according to claim 9 further comprising the step of:

providing a planar drive link to transmit power from said power source means to said feeding means.

14. A method of feeding surgical binding devices from a storage means loaded with a plurality of said binding devices and attached to a surgical instrument to a binding-device-applying-means at the working tip of said surgical instrument comprising the steps of:

providing said surgical instrument with a self-contained, energized power source means which has a power output means and is loaded with sufficient power to feed a predetermined number of the binding devices stored in said storage means;

operatively connecting said power output means to a means for feeding said binding device to the working tip;

providing a cylindrical drive link to transmit power from said power source means to said feeding means.

15. A surgical instrument comprising:

means for storing a plurality of binding devices;

means for applying at least one of said binding devices to an obect at a surgical work site;

means for feeding said binding devices at least one at a time to said applying means, said means for feeding comprising:

power source means having a power output, said power source means comprising a spring;

a feeder member means for engaging at least one of said binding devices and for moving it into a position to be acted on by said applying means;

a drive link means operatively connected to said power source means and said feeder member means for transmitting power from said power source means to said feeder member means, said drive link means comprising a cylindrical body cyclically rotatable about its axis; and means associated with said applying means for enabling said power source means to apply said power output to said drive link means at a predetermined time.

16. A surgical instrument according to claim 15 wherein said cylindrical body comprises:

an annular groove perpendicular to the axis of said body and adapted to engage an inwardly extending annular rib on a surface portion of said power source means adjacent thereto;

an annular cam groove inclined to the axis of said body and adapted to engage an inwardly extending cam connected to said feeder member means.

17. A surgical instrument comprising:

means for storing a plurality of binding devices;

means for applying at least one of said binding devices to an object at a surgical work site;

means for feeding said binding devices at least one at a time to said applying means, said means for feeding comprising:

power source means having a power output, said power source means comprising a flat, wound coil spring having a drive coil portion and a take-up portion;

a feeder member means for engaging at least one of said binding devices and for moving it into a position to be acted on by said applying means;

a drive link means operatively connected to said power source means and said feeder member means for transmitting power from said power source means to said feeder member means, said drive link comprising a flat plate cyclically reciprocable in a predetermined direction; and means associated with said applying means for enabling said power source means to apply said power output to said drive link means at a predetermined time.

18. A surgical instrument according to claim 17 further comprising a transversely extending post secured to one end of said spring and wherein said drive link comprises an aperture for mateable engagement with said post.

* * * * *